(12) United States Patent
Morrison

(10) Patent No.: US 11,571,556 B2
(45) Date of Patent: Feb. 7, 2023

(54) APPLICATOR WITH INTERNAL CHAMBERS FOR DISPENSING THERAPEUTIC FLUIDS

(71) Applicant: Christina Morrison, Claremore, OK (US)

(72) Inventor: Christina Morrison, Claremore, OK (US)

(73) Assignee: Christina Morrison, Claremore, OK (US)

( * ) Notice: Subject to any disclaimer, the term of this patent is extended or adjusted under 35 U.S.C. 154(b) by 0 days.

(21) Appl. No.: 17/605,667

(22) PCT Filed: Apr. 24, 2020

(86) PCT No.: PCT/US2020/029714
§ 371 (c)(1),
(2) Date: Oct. 22, 2021

(87) PCT Pub. No.: WO2020/219805
PCT Pub. Date: Oct. 29, 2020

(65) Prior Publication Data
US 2022/0218969 A1    Jul. 14, 2022

Related U.S. Application Data

(60) Provisional application No. 62/838,299, filed on Apr. 24, 2019.

(51) Int. Cl.
*A61F 13/40* (2006.01)
*A61F 7/03* (2006.01)
(Continued)

(52) U.S. Cl.
CPC ............ *A61M 35/006* (2013.01); *A61F 7/02* (2013.01); *A61F 7/03* (2013.01); *A61F 7/106* (2013.01);
(Continued)

(58) Field of Classification Search
CPC combination set(s) only.
See application file for complete search history.

(56) References Cited

U.S. PATENT DOCUMENTS 3,757,782 A * 9/1973 Aiken .................... A61F 13/38
604/3
4,863,422 A * 9/1989 Stanley ............... A61M 35/006
604/3
(Continued)

FOREIGN PATENT DOCUMENTS

CN        1043253 A     6/1990
CN        1387409 A    12/2002
(Continued)

OTHER PUBLICATIONS

ISA/US; PCT Search Report and Written Opinion for PCT/US2020/029714; dated Jul. 15, 2020.
(Continued)

*Primary Examiner* — Joseph A Stoklosa
*Assistant Examiner* — Adam J Avigan
(74) *Attorney, Agent, or Firm* — Crowe & Dunlevy, P.C.

(57) ABSTRACT

An applicator has a stem, one or more tips, and one or more chambers which may hold therapeutic or medicinal fluids. The applicator may be separated into two sections so the tips can be used independently. The fluids held in the chambers may be separated with one or more frangible walls which can be broken to release or mix the fluids. The tips are used as applicators for the therapeutic or medicinal effects produced by the fluids or the medicines contained in the cavity.

6 Claims, 4 Drawing Sheets

(51) Int. Cl.
*A61F 13/00* (2006.01)
*A61F 13/38* (2006.01)
*A61F 7/02* (2006.01)
*A61F 7/10* (2006.01)
*A61F 7/00* (2006.01)

(52) U.S. Cl.
CPC ........ *A61F 13/00051* (2013.01); *A61F 13/38* (2013.01); *A45D 2200/1018* (2013.01); *A61F 2007/0005* (2013.01); *A61F 2007/0006* (2013.01); *A61F 2007/0225* (2013.01)

(56) References Cited

U.S. PATENT DOCUMENTS

| | | |
|---|---|---|
| 5,120,301 A | 6/1992 | Wu |
| 5,152,742 A | 10/1992 | Simpson |
| 5,490,736 A | 2/1996 | Haber et al. |
| 6,726,386 B1 | 4/2004 | Gruenbacher et al. |
| 6,754,930 B1 * | 6/2004 | Tsaur ................. A61M 35/006 15/210.1 |
| 8,696,227 B1 | 4/2014 | Carter |
| 2002/0017310 A1 | 2/2002 | Gruenbacher et al. |
| 2004/0031114 A1 | 2/2004 | Dragan et al. |
| 2004/0165935 A1 * | 8/2004 | Kauffmann ............ A45D 34/04 401/47 |
| 2005/0049538 A1 | 3/2005 | Trevillot |
| 2006/0113318 A1 | 6/2006 | May et al. |

FOREIGN PATENT DOCUMENTS

| | | |
|---|---|---|
| CN | 108024711 A | 5/2018 |
| EP | 0397589 A1 | 11/1990 |
| EP | 2851056 A1 | 3/2015 |
| EP | 2955130 A1 | 12/2015 |

OTHER PUBLICATIONS

China National Intellectual Property Administration, Patent Application 202080029174.4, Office Action dated Jun. 30, 2022.

* cited by examiner

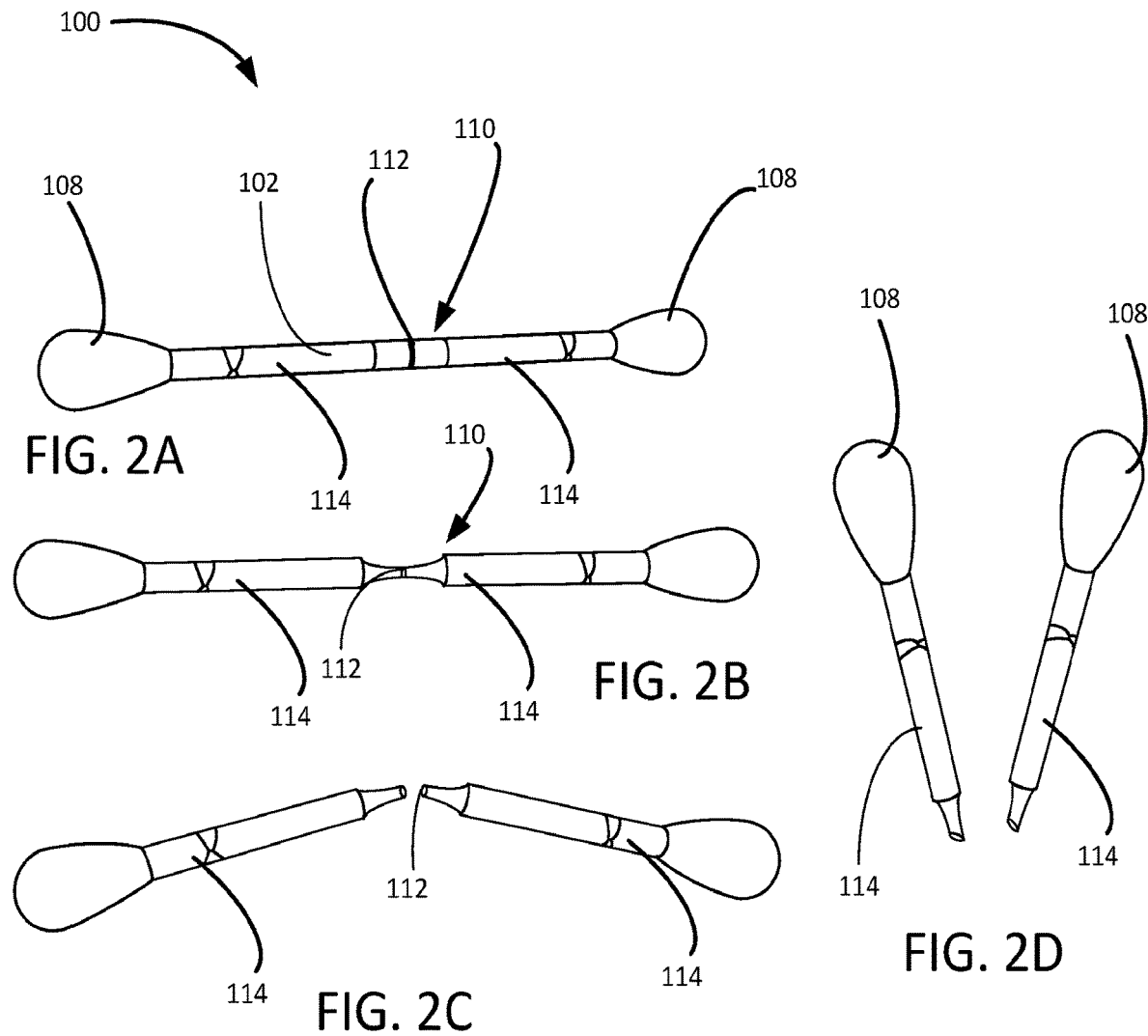

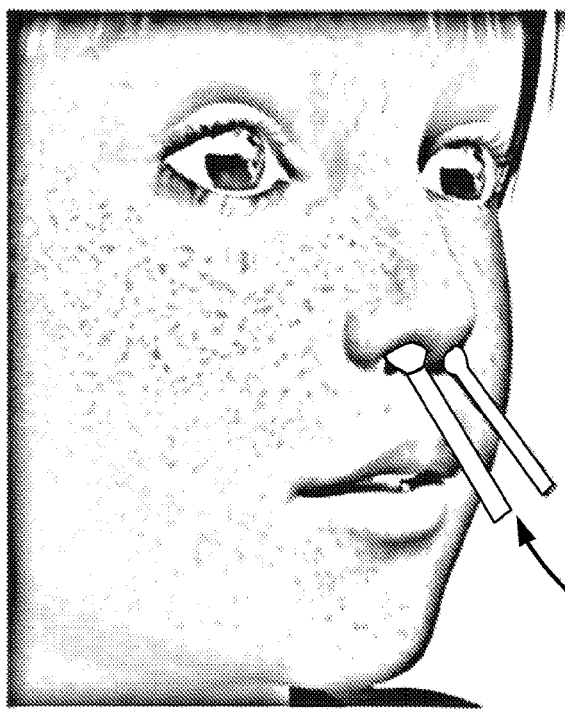
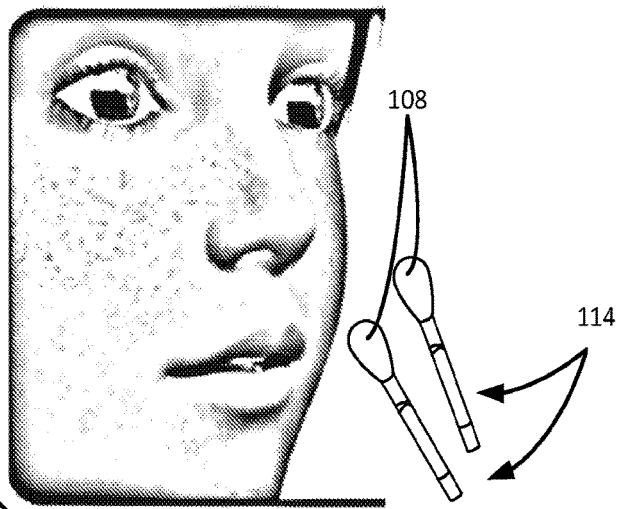
FIG. 4A
FIG. 4B
FIG. 4C

US 11,571,556 B2

APPLICATOR WITH INTERNAL CHAMBERS FOR DISPENSING THERAPEUTIC FLUIDS

RELATED APPLICATIONS

This application claims the benefit of U.S. Provisional Patent Application Ser. No. 62/838,299 filed Apr. 24, 2019 and entitled, "Ice Tips" the disclosure of which is herein incorporated by reference.

FIELD OF THE INVENTION

This invention relates generally to swabs, and more particularly, but not by way of limitation, to swabs with internal cavities for fluids.

BACKGROUND

Injuries to the body often include swelling and inflammation in the affected area, bleeding from the injury, and localized pain. Often a cold compress can be used to decrease the swelling and inflammation and slow the bleeding by restricting the blood flow. The cooling can also ease the pain by numbing the affected area. Cold compresses can easily be made with common household items, such as ice, a bag and a cloth. The cold compress can then be applied to the exterior injuries.

Internal pain, swelling and bleeding, such as those associated with the nose, ears, and mouth can be difficult to treat since the bleeding, swelling and pain occurs in hard to reach body cavities. Common cold compresses cannot be effectively applied to these internal areas or more precisely to smaller injuries due to their larger size. In addition, generally the shape and configuration of a cold compress prevents insertion into the cavities to reach the affected areas. When an injury occurs in a body cavity, the cold compress can only be applied to the closest external area to the body cavity. This external application is less effective at stopping the swelling, bleeding and pain within the internal cavity. There is, therefore, a need for an improved applicator with a size and configuration that provides a mechanism for applying therapeutics and medicines in a precise manner and in hard to reach areas of the body. It is to these and other objectives that the present invention is directed.

SUMMARY OF THE INVENTION

An applicator has a stem, a one or more tips, and one or more internal chambers which may hold treatment fluids. The treatment fluids may be separated by a common frangible wall. The frangible wall can be broken to mix treatment fluids or can allow for separate application of the treatment fluids. The mixing of the treatment fluids can produce therapeutic effects, such as cooling or warming. The tip provides a means of applying the therapeutic effects or treatment fluids to areas that may have bleeding, swelling, or pain. The applicator can be held by the stem to allow the tip to be maneuvered into body cavities and hard to reach areas of the body. In some embodiments the applicator may be separated into two separate applicators or stem stubs.

BRIEF DESCRIPTION OF THE DRAWINGS

FIGS. 2A-2D present various views of the applicator of FIG. 1 being separated into two stem stubs.

FIGS. 4A-4C present examples of methods of using the applicator of FIG. 1.

WRITTEN DESCRIPTION

In exemplary embodiments, a therapeutic applicator includes a hollow stem that contains two or more internal chambers that are each separated by a common frangible wall. The internal chambers are configured to contain one or more treatment fluids. In some embodiments, the applicator contains two different fluids that undergo a chemical reaction when mixed. The reactive fluids are contained within separate chambers until the frangible wall is ruptured by applying an external force to the hollow stem proximate the frangible wall. In some embodiments, the frangible wall can be ruptured by bending or compressing the stem. Once the frangible wall has been compromised, the reactive fluids are permitted to mix within the now-connected internal chambers.

In some embodiments, the reactive fluids undergo an endothermic reaction in which the temperature of the reacting fluids decreases for use in cold therapy applications. In other embodiments, the reactive fluids undergo an exothermic reaction in which the temperature of the reacting fluids increases for use in warm therapy applications. In these embodiments, the applicator is optimally provided with one or more applicator tips that facilitate heat transfer from the internal reacted fluids to the treatment subject through the external applicator tip. The applicator tips and stem may be provided in a number of sizes and configurations, including embodiments in which the applicator tips are sized and configured to permit placement of the applicator tip on internal or small treatment areas that are difficult to reach with conventional hot and cold compresses that are larger and less accurate. In these embodiments, the applicator is uniquely suited for applying a focused therapeutic effect inside a person's nose, ear or mouth.

In some embodiments, the applicator is also configured to be separated into two portions that each includes a stem and applicator tip. In these embodiments, each stem portion includes a plurality of internal fluid-containing chambers that are separated by a frangible wall. In yet other embodiments, the applicator includes a porous applicator tip that is configured to dispense a fluid from within the stem.

Figure 1:
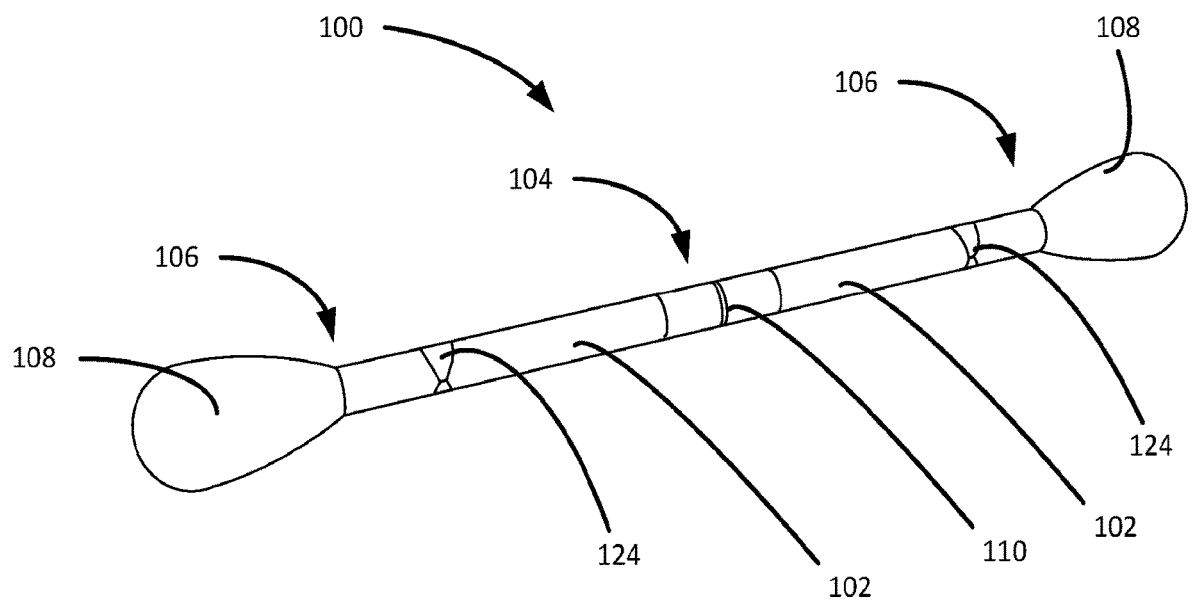
FIG. 1 is a perspective view of an applicator constructed in accordance with an exemplary embodiment.

Referring now to FIG. 1, shown therein is a perspective view of an applicator 100 constructed in accordance with an exemplary embodiment. In this embodiment, the applicator 100 has an elongate tubular stem 102 with a central portion 104, and two distal ends 106 located at opposing ends of the stem 102. The applicator 100 includes applicator tips 108 attached to the distal ends 106 of the stem 102. In some embodiments, the stem 102 is cylindrical and manufactured from a plastic, treated paper, or composite material. In most embodiments, the applicator tips 108 are composed of a sponge-like material or synthetic or natural fibrous materials, such as cotton.

Turning to FIGS. 2A-2D, the applicator 100 optionally includes a separable joint 110 that is configured to break apart when exposed to bending, compressive or tensile forces. The separable joint 110 includes a breakable connecting face 112. The breakable connecting face 112 may be perforated or otherwise weakened during manufacture to permit the separable joint 110 to be separated by hand without the use of implements. In some embodiments, the separable joint 110 is manufactured from a material that initially exhibits a semi-elastic response to deformation stress to a yield point that exhibits brittleness. As depicted in FIG. 2B, the application of tensile stress draws out the separable joint 110 under an elastic deformation. When a bending force is then applied (in FIG. 2C), the embrittled separable joint 110 breaks and the stem 102 separates into two stem stubs 114 that each extend from a proximal end 116 near the separable joint 110 to the distal end 106 (as depicted in FIGS. 2C and 2D).

In the embodiment depicted in FIGS. 2A-2D, the separable joint 110 is located within the central portion 104, but it will be understood that the separable joint 110 may be placed elsewhere within the applicator 100. It will be further appreciated that in some embodiments the applicator 100 will not include the separable joint 110.

Figure 3A:
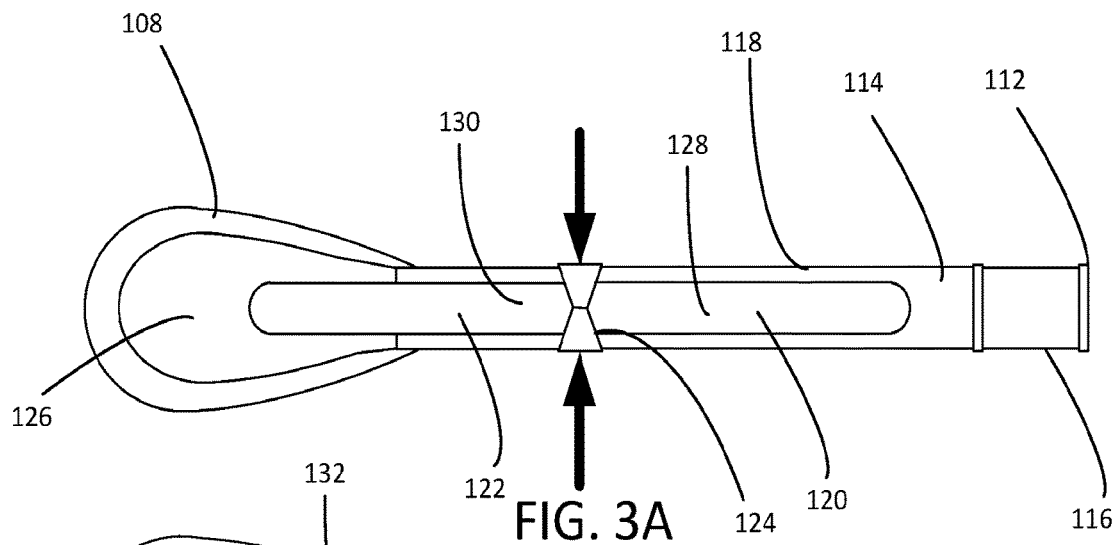
FIGS. 3A-3B depict the process of opening a frangible wall within the applicator to permit mixing of reactive fluids within the applicator stem.

Turning to FIG. 3A, shown therein is a partial cross-sectional view of one of the stem stubs 114 after the separable joint 110 has been broken to separate the stem 102 into two stem stubs 114 (only one stem stub 114 is depicted in FIG. 2). Each stem stub 114 includes an outer wall 118, a proximal fluid chamber 120, a distal fluid chamber 122 and a frangible wall 124. The proximal fluid chamber 120 and the distal fluid chamber 122 are contained within the outer wall 118. The frangible wall 124 separates the proximal fluid chamber 120 from the distal fluid chamber 122. In some embodiments, the proximal fluid chamber 120 extends within the outer wall 118 between the proximal end 116 and the frangible wall 124, and the distal fluid chamber 122 extends from the frangible wall 124 to the distal end 106. Thus, in many embodiments the applicator 100 includes first and second proximal fluid chambers 120 and first and second distal fluid chambers 122, where the first proximal and distal fluid chambers 120 are in a first stem stub 114 and the second proximal and distal fluid chambers 122 are in a second stem stub 114.

In the embodiment depicted in FIG. 3A, the distal fluid chamber 122 extends beyond the distal end 106 of the stem stub 114 into a tip cavity 126 within the applicator tip 108. In other embodiments, an additional frangible wall is positioned between the distal fluid chamber 122 and the tip cavity 126. In some embodiments, the tip cavity 126 and distal fluid chamber 122 constitute a single, unitary, unsegmented chamber. In most embodiments, the tip cavity 126 is also made from an impermeable plastic, treated paper or composite materials. In embodiments in which the applicator 100 is intended to dispense a single therapeutic fluid or mixture of fluids, however, the tip cavity 126 is constructed from a permeable, porous material that allows the therapeutic fluid to pass out of the tip cavity 126 into the surrounding applicator tip 108. In these embodiments, the frangible wall 124 may be positioned closer to the tip cavity 126 to increase the volume within the proximal fluid chamber 120 for the single therapeutic fluid.

Figure 3B:
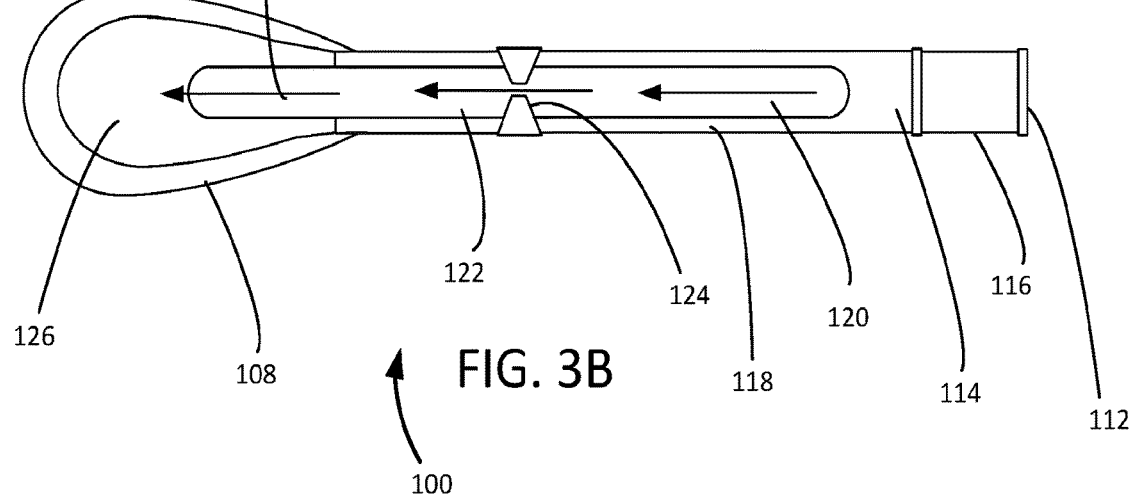

The frangible wall 124 can be ruptured by applying a compressive or bending force to the frangible wall 124 (as depicted in FIG. 3A). Once the frangible wall 124 has been ruptured (as depicted in FIG. 3B), the proximal fluid chamber 120 is placed into fluid communication with the distal fluid chamber 122. In the embodiments depicted in FIGS. 3A and 3B, the frangible wall 124 includes a tapered middle portion that can be easily broken to permit the exchange of fluids between the adjacent proximal and distal fluid chambers 120, 122. In some applications, it may be necessary or helpful to shake the applicator 100 after the frangible wall 124 has been ruptured to increase or expedite the mixing of the first and second fluids 128, 130. In other embodiments the frangible wall 124 may include a simple valve port constructed from an elastic or semi-elastic material that opens when a compressive force is applied to the frangible wall 124, but closes when the compressive force is removed. In some embodiments, the valve port includes a flapper element that rests onto a valve seat until a compressive force deforms the flapper element or valve seat to temporarily open the valve port.

In some embodiments, the proximal and fluid chambers 120, 122 are configured to contain fluids that undergo a chemical reaction when mixed. In some embodiments, a first fluid 128 contained within the proximal fluid chamber 120 and a second fluid 130 within the distal fluid chamber 122 undergo an endothermic or exothermic reaction when the first and second fluids 128, 130 are mixed to create a fluid mixture 132. An endothermic reaction reduces the temperature of the fluid mixture 132 for providing cold therapeutic treatments with the applicator 100. An exothermic reaction increases the temperature of the fluid mixture 132 for providing warm therapeutic treatments. In each case, the first and second fluids 128, 120 may be selected from any commercially available chemicals that are non-toxic and generally safe for therapeutic applications. For endothermic (cooling) reactions, water and either ammonium nitrate or ammonium chloride may be selected as the first and second fluids 128, 130. For exothermic (heating) reactions, water and calcium chloride may be selected as the first and second fluids 128, 130.

In other applications, the applicator 100 is intended to dispense a therapeutic fluid through the applicator tips 108. Suitable applications include dispensing sterilizing, analgesic, or styptic medicines. In these embodiments, the tip cavity 126 is porous or fluid-permeable to permit fluid to be dispensed from the tip cavity 126 through the applicator tip 108. It will be appreciated that the therapeutic fluid can be contained within the proximal fluid chamber 120 until the frangible wall 124 is ruptured, thereby permitting the fluid to move from the proximal fluid chamber 120 into the tip cavity 126, either directly or through the distal fluid chamber 122 if the embodiment of the applicator 100 includes the distal fluid chamber 122. For applications in which the therapeutic fluid includes volatile components, such as isopropyl alcohol, the applicator 100 provides a mechanism for keeping the therapeutic fluid in the sealed proximal fluid chamber 120 until the applicator 100 is used. In some embodiments, the medicinal fluid in the first and second proximal fluid chambers 120 is the same. In other embodiments, the medicinal fluids contained within the first and second proximal fluid chambers 120 are not the same. In some embodiments, it may be desirable to include a first medicinal fluid (such as a wound cleaning solution) in the first proximal fluid chamber 120 and a second medicinal fluid (such as a styptic or coagulation agent) in the second proximal fluid chamber 120.

Turning to FIGS. 4A-4C, shown therein are various depictions of potential uses of the applicator 100 in providing a therapeutic treatment to a subject. In the embodiments in which the applicator 100 is used to provide targeted cold therapy, the frangible wall 124 is ruptured or opened through the application of an external force and the fluids in the proximal and fluid chambers 120, 122 are mixed to initiate the endothermic reaction. The cool fluid mixture 132 is transferred to the tip cavity 126, where it cools the applicator tip 108. The cooled applicator tip 108 can then be accurately applied to areas of the body and internal cavities such as a nostril, mouth, or ear canal to treat symptoms including pain, swelling and bleeding. The stem stubs 114 can be used to hold the applicator 100 as the applicator tip 108 is applied to the targeted area. After the injury has been treated or the cooling effects have subsided, the user can dispose of the applicator 100. It will be noted that the applicator 100 has been separated at the separable joint 110 in FIGS. 4A and 4B, but the applicator 100 has not been separated into two stem stubs 114 in FIG. 4C.

It is to be understood that even though numerous characteristics and advantages of various embodiments of the present invention have been set forth in the foregoing description, together with details of the structure and functions of various embodiments of the invention, this disclosure is illustrative only, and changes may be made in detail, especially in matters of structure and arrangement of parts within the principles of the present invention to the full extent indicated by the broad general meaning of the terms in which the appended claims are expressed. It will be appreciated by those skilled in the art that the teachings of the present invention can be applied to other systems without departing from the scope and spirit of the present invention.

What is claimed is:

1. An applicator for providing a therapeutic remedy to a living subject, the applicator comprising:
    a stem, wherein the stem comprises:
        a central portion;
        a pair of distal ends at opposite ends of the stem;
        a separable joint within the central portion;
        a first proximal fluid chamber inside the stem on a first side of the separable joint;
        a first distal fluid chamber inside the stem of the first side of the separable joint;
        a first frangible wall inside the stem between the first proximal fluid chamber and the first distal fluid chamber, wherein the first frangible wall is configured to be ruptured by the application of an external compressive force on the stem proximate the first frangible wall;
        a second proximal fluid chamber inside the stem on a second side of the separable joint;
        a second distal fluid chamber inside the stem on the second side of the separable joint;
        a second frangible wall inside the stem between the second proximal fluid chamber and the second distal fluid chamber, wherein the second frangible wall is configured to be ruptured by the application of an external compressive force on the stem proximate the second frangible wall;
        a first fluid contained with the first and second proximal fluid chambers;
        a second fluid contained with the first and second distal fluid chambers; and
        wherein the first fluids and second fluids are reactive when mixed to form a fluid mixture within each of the first and second proximal and distal fluid chambers.

2. The applicator of claim 1, wherein the first fluid and second fluid undergo an endothermic reaction when mixed.

3. The applicator of claim 2, wherein one of the first and second fluids is selected from the group consisting ammonium nitrate and ammonium chloride, and wherein the other of the first and second fluids is water.

4. The applicator of claim 1, wherein the first fluid and second fluid undergo an exothermic reaction when mixed.

5. The applicator of claim 4, wherein one of the first and second is water and the other of the first and second fluids is calcium chloride.

6. The applicator of claim 1, wherein the separable joint is configured to permit the separation of the stem into first and second stem stubs.

\* \* \* \* \*